United States Patent
Watanabe et al.

(10) Patent No.: US 7,465,535 B2
(45) Date of Patent: Dec. 16, 2008

(54) DEHYDRATION PROCEDURES FOR INDUCTION OF CRYPTOBIOSIS IN INSECT LARVAE

(75) Inventors: Masahiko Watanabe, deceased, late of Ibaraki (JP); by Kazuyo Watanabe, legal representative, Tsukuba (JP); Takashi Okuda, Tsukuba (JP); Takahiro Kikawada, Tsukuba (JP); Yasuhiko Kobayashi, Takasaki (JP); Tetsuya Sakashita, Takasaki (JP); Seichi Wada, Takasaki (JP); Tomoo Funayama, Takasaki (JP)

(73) Assignee: National Institute of Agrobiological Sciences, Tsukuba-shi (JP)

( * ) Notice: Subject to any disclaimer, the term of this patent is extended or adjusted under 35 U.S.C. 154(b) by 329 days.

(21) Appl. No.: 11/150,268

(22) Filed: Jun. 13, 2005

(65) Prior Publication Data
US 2006/0160061 A1    Jul. 20, 2006

(30) Foreign Application Priority Data
Jun. 11, 2004    (JP)    ............................. 2004-173561

(51) Int. Cl.
*A01N 1/00*    (2006.01)
*A01K 67/00*    (2006.01)
*G09B 23/36*    (2006.01)

(52) U.S. Cl. .............................. 435/1.1; 800/8; 434/295
(58) Field of Classification Search .................. 435/1.1
See application file for complete search history.

(56) References Cited

U.S. PATENT DOCUMENTS
2004/0185425 A1 *    9/2004    Okuda et al. .................. 435/1.1

OTHER PUBLICATIONS
Watanabe et al., J Experimental Biol., 2003, 206, 2281-2286.*
Hinton et al., Nature, Oct. 1960, vol. 188, p. 336-337.*

* cited by examiner

*Primary Examiner*—Lora E Barnhart
(74) *Attorney, Agent, or Firm*—Oblon, Spivak, McClelland, Maier & Neustadt, P.C.

(57) ABSTRACT

This invention provides a method for effectively producing dehydrated larvae for educational materials without disrupting the environment. The cryptobiotic larvae for educational materials can be obtained by dehydrating larvae while gradually reducing humidity in 3 separate stages.

10 Claims, 7 Drawing Sheets

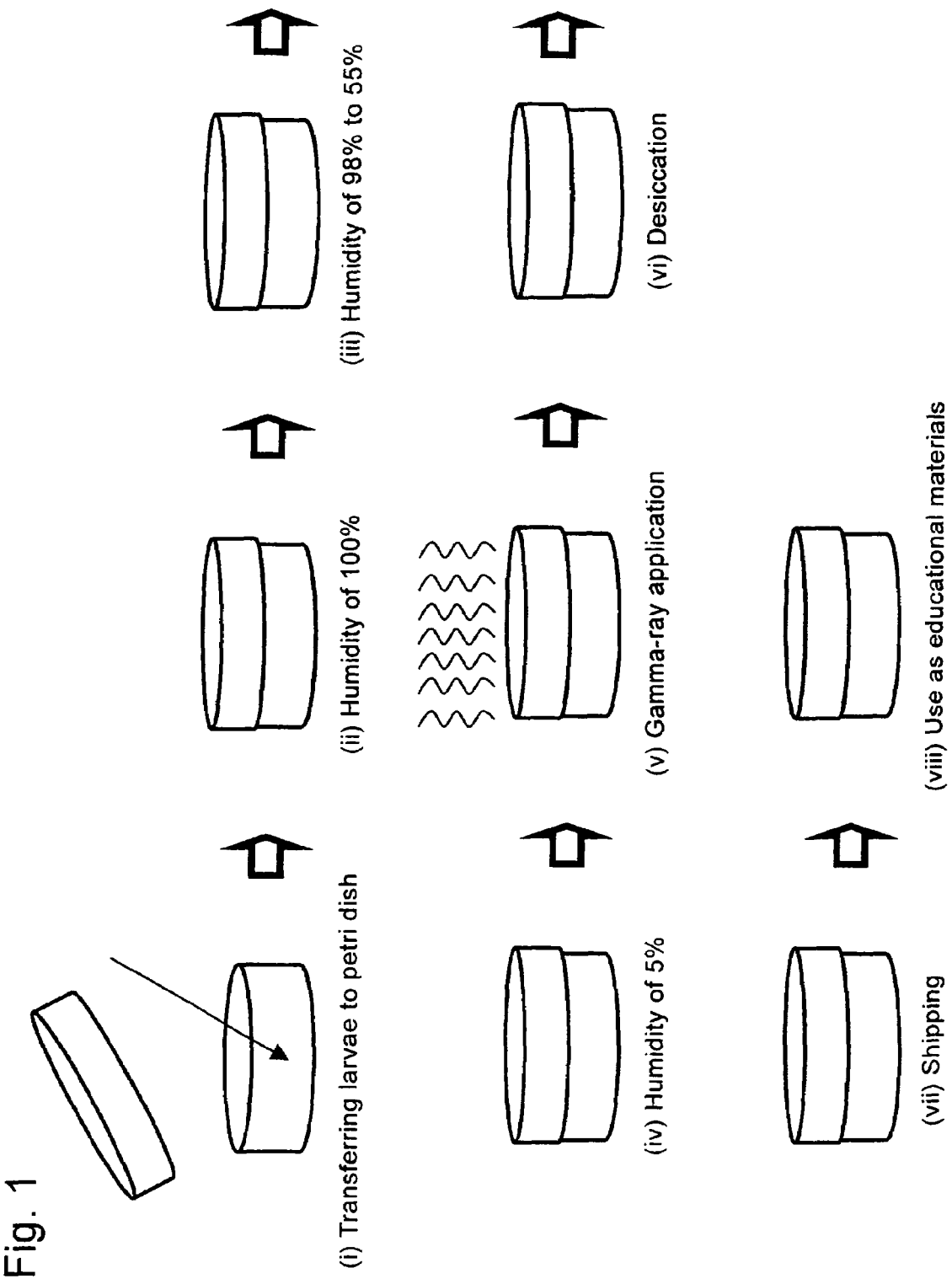

DEHYDRATION PROCEDURES FOR INDUCTION OF CRYPTOBIOSIS IN INSECT LARVAE

TECHNICAL FIELD

The present invention relates to dehydration procedures for induction of cryptobiosis in insect larvae. More particularly, the present invention relates to a method for effectively dehydrating insect larvae without disrupting the environment, even when insect larvae are revived to be utilized as educational materials.

BACKGROUND ART

In the past, dehydrated larvae of the *Polypedilum vanderplanki* had been prepared in the following manner. Specifically, a piece of filter paper and 440 µl of distilled water were put in a dehydration vessel (a glass petri dish with a diameter of 6 cm) with approximately 10 larvae, the dehydration vessel was set in a desiccator with humidity of 5% or lower, and the content of the desiccator was subjected to dehydration for a period of two days. However, dehydrated larvae often stuck to filter paper or a glass surface, and their bodies were often damaged when they were collected from the dish. Such larvae died from blood loss when they were rehydrated. Since this procedure required careful handling of insect larvae one by one, an extremely long period of time was needed in order to recover a large quantity of larvae.

When a large number of dehydrated larvae were transferred to another vessel, those larvae would not stick to the wall or the like in the vessel. Accordingly, the dehydrated larvae they faced possible physical damage due to oscillation caused upon transportation of the larvae-containing vessel.

The applicant of the present application has filed for a patent "a method for dehydrating and preserving tissues of multicellular organisms at ordinary temperature" (JP Patent Application No. 2003-72585). This invention has been completed with the discovery of conditions for inducing drought dormancy and conditions for dehydration, wherein tissues of multicellular organisms, particularly those of *Polypedilum vanderplanki*, are gradually dehydrated while culturing to achieve a state of complete dehydration and then rehydrated to recover from cryptobiosis.

With this technique, however, cryptobiotic larvae could not be effectively produced within a short period of time.

*Polypedilum vanderplanki* inhabits Africa exclusively and lives exclusively in small puddles in rocky areas. Since they are very susceptible to natural enemies or interspecies competition, they cannot propagate themselves in large puddles or ponds that are wet all year round (McLachlan, A., 1983, Life-history tactics of rain-pool dwellers, Journal of Animal Ecology 52: 545-561). When adult insects escape from a laboratory in Japan, however, the possibility that they would propagate themselves cannot be completely denied. In such a case, they could significantly affect the indigenous ecosystem.

Use of larvae of *Polypedilum vanderplanki* as educational materials has been attempted. In order to realize such attempt, it is required to supply sufficiently dehydrated larvae so that they can be easily utilized as educational materials or the like. At the same time, the risk of ecosystem disruption must be avoided in case such larvae escape. Thus, there remain many problems to be resolved, as mentioned above.

SUMMARY OF THE INVENTION

It is an object of the present invention to develop a method for effectively producing cryptobiotic insect larvae to be utilized as educational materials or the like without disrupting the environment.

The present inventors have conducted concentrated studies in order to attain the above object. As a result, they found that cryptobiotic insect larvae for educational materials could be obtained by gradually reducing humidity in 3 separate stages to dehydrate the insect larvae.

Specifically, the present invention relates to:

(1) dehydration procedures for induction of cryptobiosis in insect larvae comprising gradually reducing humidity to dehydrate insect larvae contained in a vessel;

(2) the dehydration procedures according to (1), wherein humidity is reduced in 3 separate stages;

(3) the dehydration procedures according to (2), wherein humidity is kept at 100% for 1 day, 98% to 55% for 1 day, and 5% or lower for 1 day or longer;

(4) the dehydration procedures according to any of (1) to (3), wherein a gamma ray of 50 gray or higher is applied after dehydration; and (5) the dehydration procedures according to any of (1) to (4), wherein the insect larvae are *Polypedilum vanderplanki*.

A system wherein procedures including dehydration, sterilization, preservation, shipping, and induction of cryptobiosis are carried out in a single vessel has been developed to completion (FIG. 1 and FIG. 2). In the present invention, a plastic petri dish was used as such vessel.

More specifically, larvae are first put in the petri dish, humidity is kept at 100% for 1 day, humidity is then reduced to and maintained at 98% to 55% for 1 day, and the larvae are subjected to dehydration at humidity of 5% or lower for 1 day or longer, as shown in FIG. 1. Thereafter, the larvae are irradiated with a gamma ray for sterilization, desiccated, shipped, and then utilized as educational materials or the like.

When larvae are completely dehydrated, water constituting 80% of the body is lost, as shown in FIG. 2. This shortens the length, width, and thickness of larvae (A: before dehydration; B: after complete dehydration).

In the present invention, "dehydration procedures for induction of cryptobiosis" are aimed at cryptobiosis following dehydration. This enables close observation of the ecology of insects as educational materials.

The dehydration procedures for induction of cryptobiosis according to the present invention have a variety of benefits as follows.

(1) The procedures can eliminate operations of recovering larvae from one vessel and transferring them to another vessel. This can shorten the time required for operation and significantly reduce the risk of damaging larvae.

(2) The procedures can allow a method that does not involve the use of filter paper when dehydrating larvae in the petri dish. When filter paper is not used via a conventional technique (i.e., a method wherein filter paper and 440 µl of distilled water are added to the dehydration vessel and larvae are dehydrated at humidity of 5% or lower over a period of 2 days), distilled water droplets gather in part of the vessel. Thus, conditions of larvae vary widely depending on the spots in which they were dehydrated. This results in an increased number of larvae that are not cryptobiotically dehydrated.

Cryptobiotically dehydrated larvae can be obtained with a high probability without the use of filter paper or distilled water. This can be realized by placing the petri dish in a large vessel and effectively controlling the relative humidity in the vessel.

Dehydration without the use of filter paper can result in the following benefits, for Example; 1) labor and cost associated with the use of filter paper can be omitted; 2) the risk of damaging larvae via movement of filter paper in the vessel during transportation can be avoided; and 3) observation is not disturbed when larvae are rehydrated to induce cryptobiosis.

(3) Adoption of a method involving application of a gamma ray to the entirety of a vessel containing dehydrated larvae stuck therein to prepare sterilized and dehydrated larvae can eliminate operations such as recovery or transportation of larvae. Also, establishment of a sterilization technique can avoid the risk of ecosystem disruption.

(4) Dehydrated larvae are thinly stretched and stuck on the bottom of the vessel. Thus, larvae hardly fall off even when the vessel is vigorously shaken, which can reduce the risk of damaging larvae in the vessel during transportation. When the dehydrated larvae are sterilized via gamma ray application, transferred to a location for preservation thereafter, and then shipped, each such procedure requires transportation of samples. Accordingly, it is very important to reduce the risk of damaging larvae during transportation.

(5) When shipment of larvae is attempted with the use of a smaller tubular vessel, for example, it is difficult to observe the way of recovery if the larvae are rehydrated in such state. This would also cause trouble for a purchaser in terms of the necessity of preparing an additional vessel for observation, and produce a risk of damaging larvae upon transportation thereof to the observation vessel. This problem can be resolved via the use of a plastic petri dish with a diameter of approximately 5 cm, since such dish is also suitable for observation.

(6) Use of a plastic vessel is advantageous since it is much lighter, less breakable, and less expensive than vessels made of glass or other materials.

Among numerous insects, an insect species that is exceptionally tolerant to dehydration stress and lives in dry regions in Africa, i.e., *Polypedilum vanderplanki*, was selected for dehydrated insect educational materials.

Larvae of *Polypedilum vanderplanki* are tolerant to desiccation for a long period of time (for up to 17 years) (Adams, A., 1985, Cryptobiosis in Chironomidae (Diptera) two decades on. Antenna: Bulletin of the Royal Entomological Society of London 8:58-61), and dehydrated larvae have exceptionally high stress tolerance. Specifically, they are revived and then become to be able to swim after rehydration, even when they are subjected to high-temperature treatment at 103° C., low-temperature treatment at –270° C., or treatment with 100% ethanol (Hinton, H. E., 1960. Cryptobiosis in the larva of *Polypedilum vanderplanki* Hint. (Chironomidae)). Journal of Insect Physiology 5:286-300). While *Polypedilum vanderplanki* are in the larval stage, they can enter cryptobiotic state repeatedly (Hinton, H. E., 1960. Cryptobiosis in the larva of *Polypedilum vanderplanki* Hint. (Chironomidae)). Thus, larvae of *Polypedilum vanderplanki* can serve as excellent educational materials since their exceptional tolerance to various types of stresses and the way that they are revived can be clearly observed.

BRIEF DESCRIPTION OF THE DRAWINGS

FIG. 1 schematically shows a system wherein procedures including dehydration, sterilization, preservation, shipping, and induction of cryptobiosis of larvae are carried out in a single plastic vessel.

PREFERRED EMBODIMENTS OF THE INVENTION

The present invention is described in greater detail with reference to the Examples, although the present invention is not limited thereto.

Example 1

Conditions for Dehydrating Larvae in a Plastic Petri Dish via Humidity Control

The present inventors carried out the following experiment in order to determine the conditions for dehydrating the larvae of *Polypedilum vanderplanki* within as short a time frame as possible by controlling the relative humidity in a 5-cm plastic vessel.

1. Approximately 10 larvae of *Polypedilum vanderplanki* were put in a plastic petri dish.

2. The petri dish was placed in a large vessel, the relative humidity therein was set at various levels, the petri dish was finally transferred to a desiccator with humidity of 5%, and dehydration was carried out for 1 day or longer.

Figure 2A:
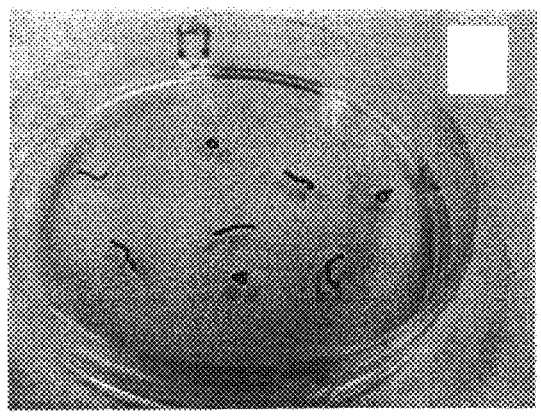
FIG. 2 shows larvae before dehydration (a) and after complete dehydration (b) in a plastic petri dish.
Figure 2B:
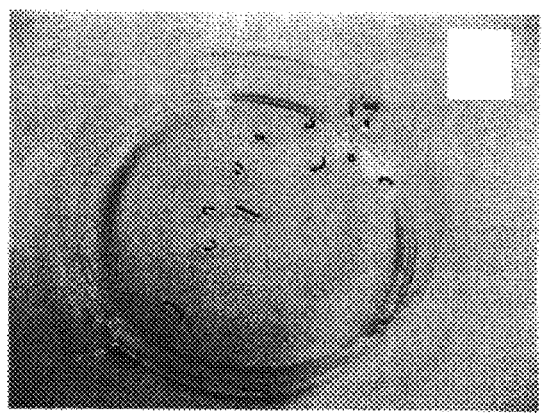
Figure 3:
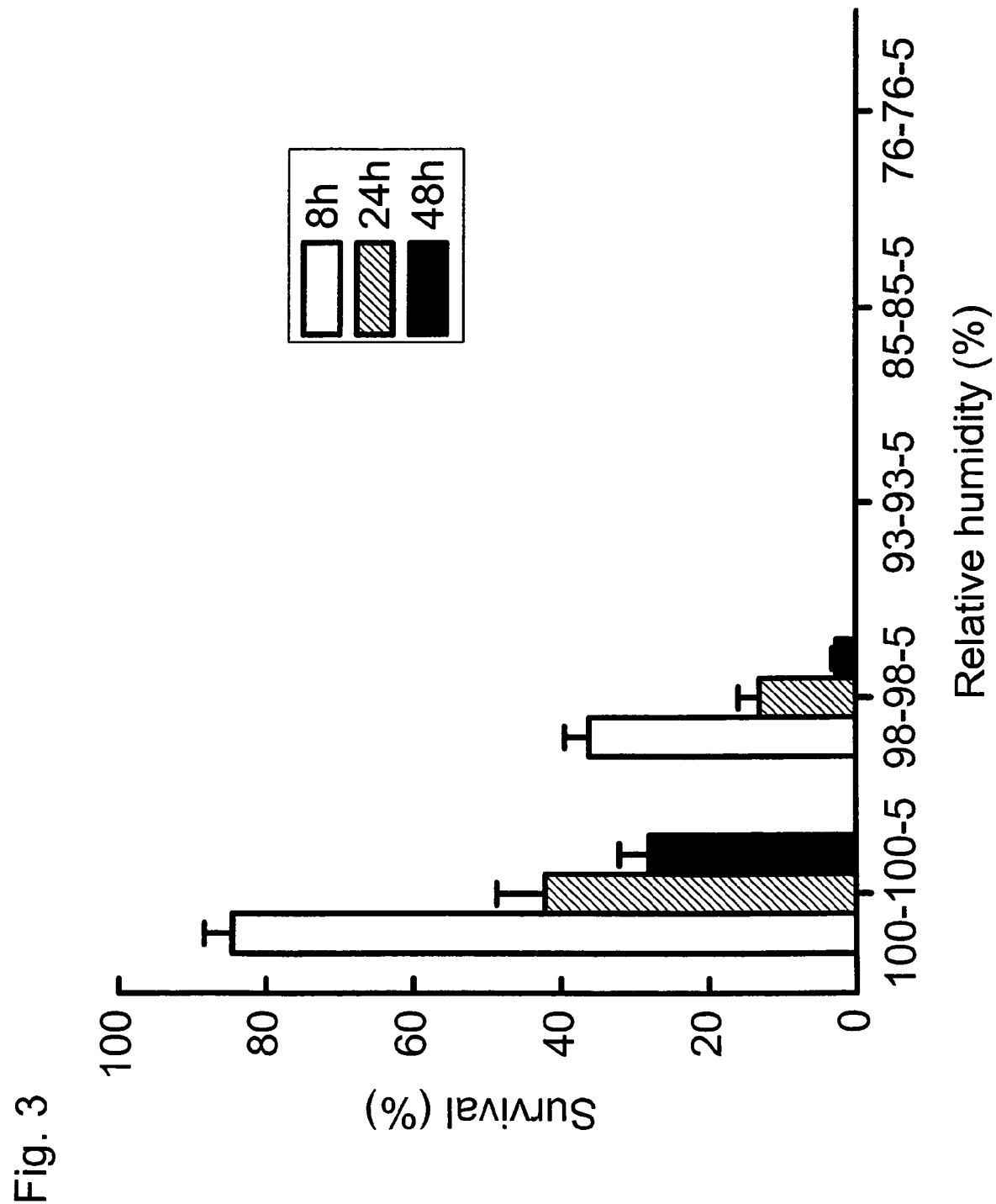
FIG. 3 shows comparison of the results of dehydrating larvae using a plastic petri dish under 2-stage dehydration conditions.

As shown in FIG. 3, only several percents of larvae had survived 48 hours later when they were dehydrated under 2-stage humidity conditions, i.e., 98%-98%-5%. When they were dehydrated under conditions of 100%-100%-5%, approximately 30% of larvae were found to have survived 48 hours later.

Figure 4:
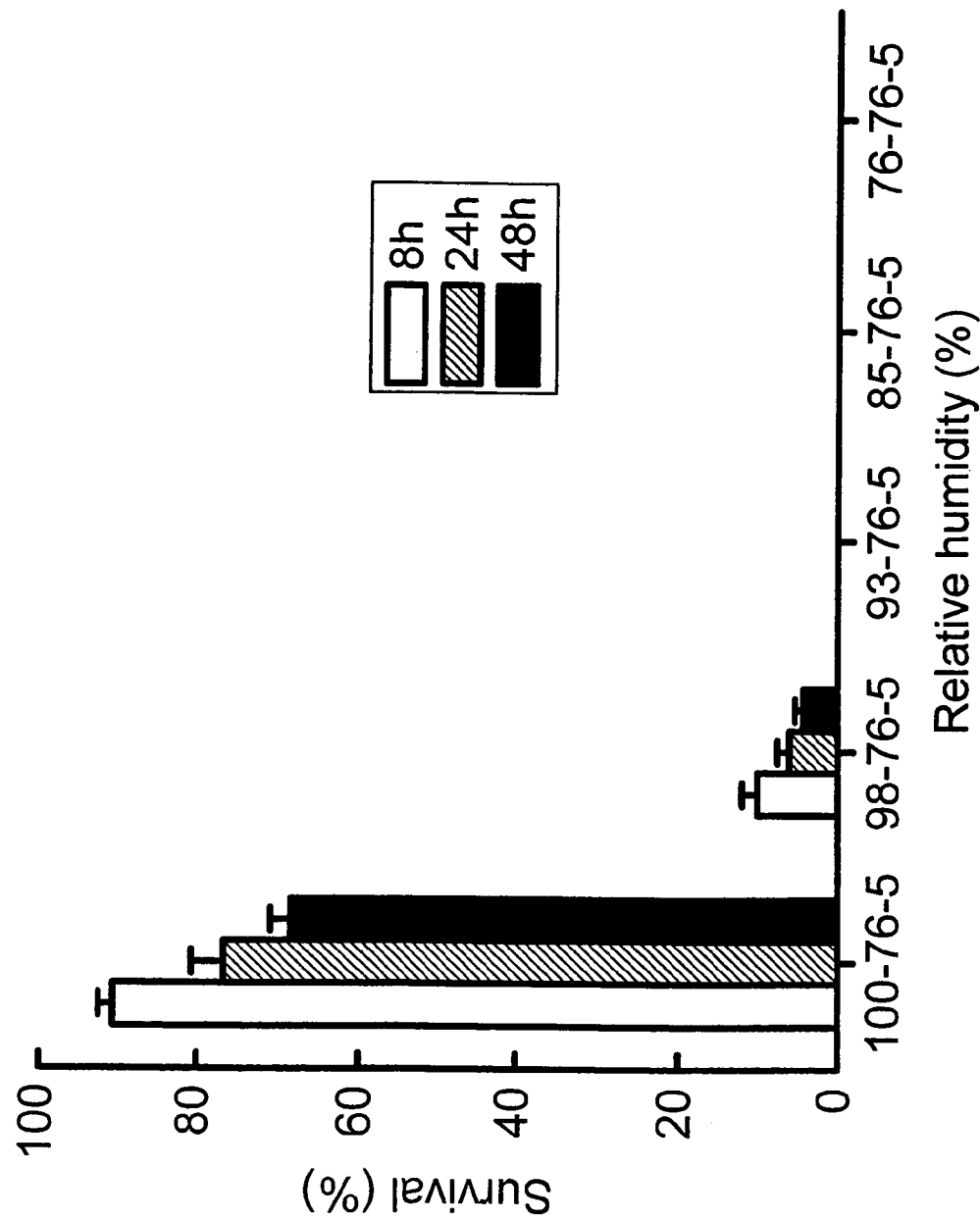
FIG. 4 shows comparison of the results of dehydrating larvae using a plastic petri dish under 3-stage dehydration conditions with humidity change in the first stage.

As is apparent from FIG. 4, even though they were dehydrated under 3-stage humidity conditions, the survival ratio was reduced to a great extent if humidity at the first stage was lower than 100%.

Figure 5:
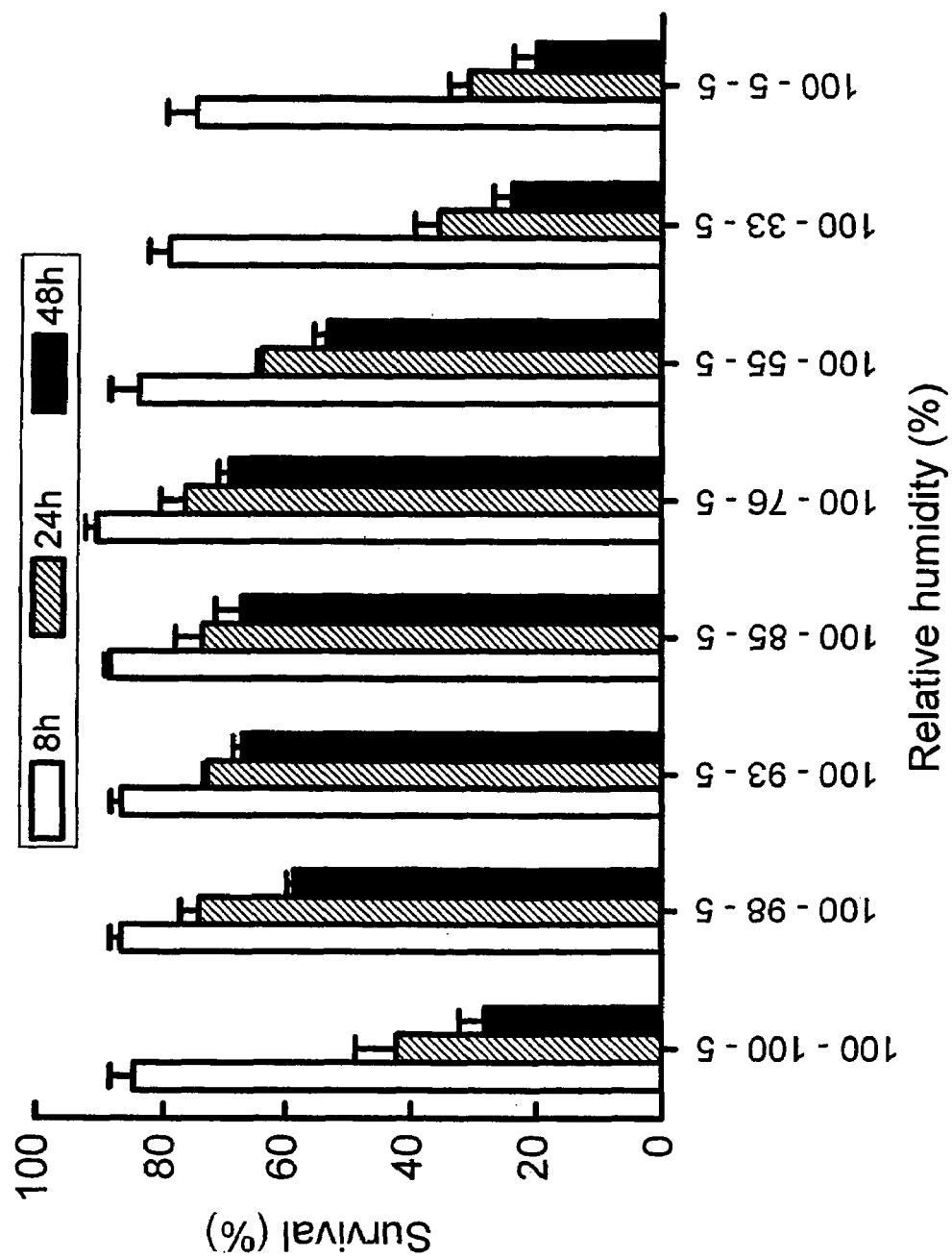
FIG. 5 shows comparison of the results of dehydrating larvae using a plastic petri dish under 3-stage dehydration conditions.

When the humidity conditions were set in 3 separate stages and the first stage was set at 100%, the survival ratio 48 hours later would exceed 50% when the second stage had been set at 55% to 98%. Conditions where humidity is kept at 100% for 1 day, 76% for 1 day, and 5% for 1 day produce the best larval survival ratio (approximately 70%), as is apparent from FIG. 5. The duration of dehydration at the third stage is preferably 1 day, although it may be longer than 1 day.

Figure 6:
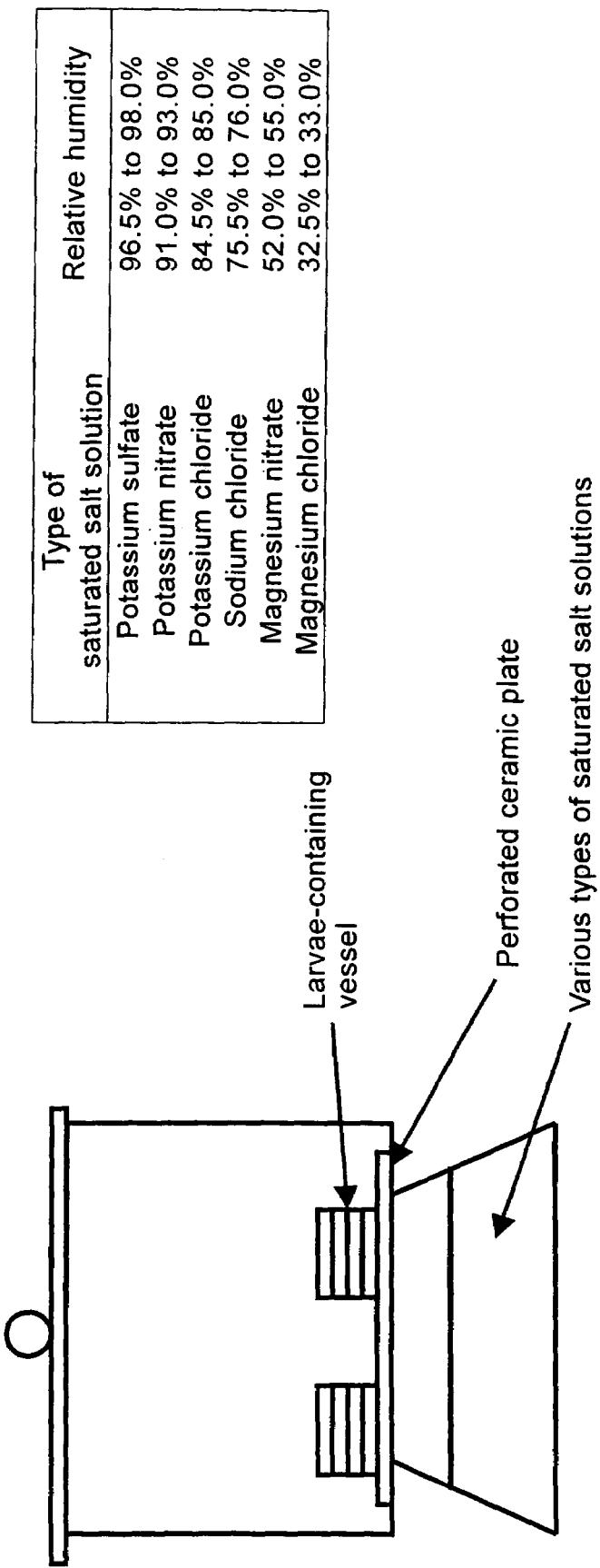
FIG. 6 shows the method for controlling humidity with the use of a saturated salt solution.

A saturated salt solution was used for such relative humidity control. Spaces at the bottom of the large vessel shown in FIG. 6 were filled with an adequate saturated salt solution in accordance with the relative humidity of each vessel to maintain the relative humidity in spaces around the larvae-containing vessel at a constant level. A relative humidity of 100% was realized by filling the spaces at the bottom of the large vessel with water.

Example 2

Influence of Gamma-Ray Application on Larvae of *Polypedilum vanderplanki*

The present inventors carried out the following experiment in order to examine the influence of gamma ray application on the growth or propagation of the larvae of *Polypedilum vanderplanki*.

1. A gamma ray of 1 to 3,000 gray was applied to the entire vessel containing the larvae dehydrated in the plastic petri dish.

2. The larvae to which gamma rays had been applied were rehydrated, and the survival ratio, the pupation rate, the eclosion rate, and the occurrence of propagation of larvae 48 hours later were inspected.

Figures 7A, 7B:
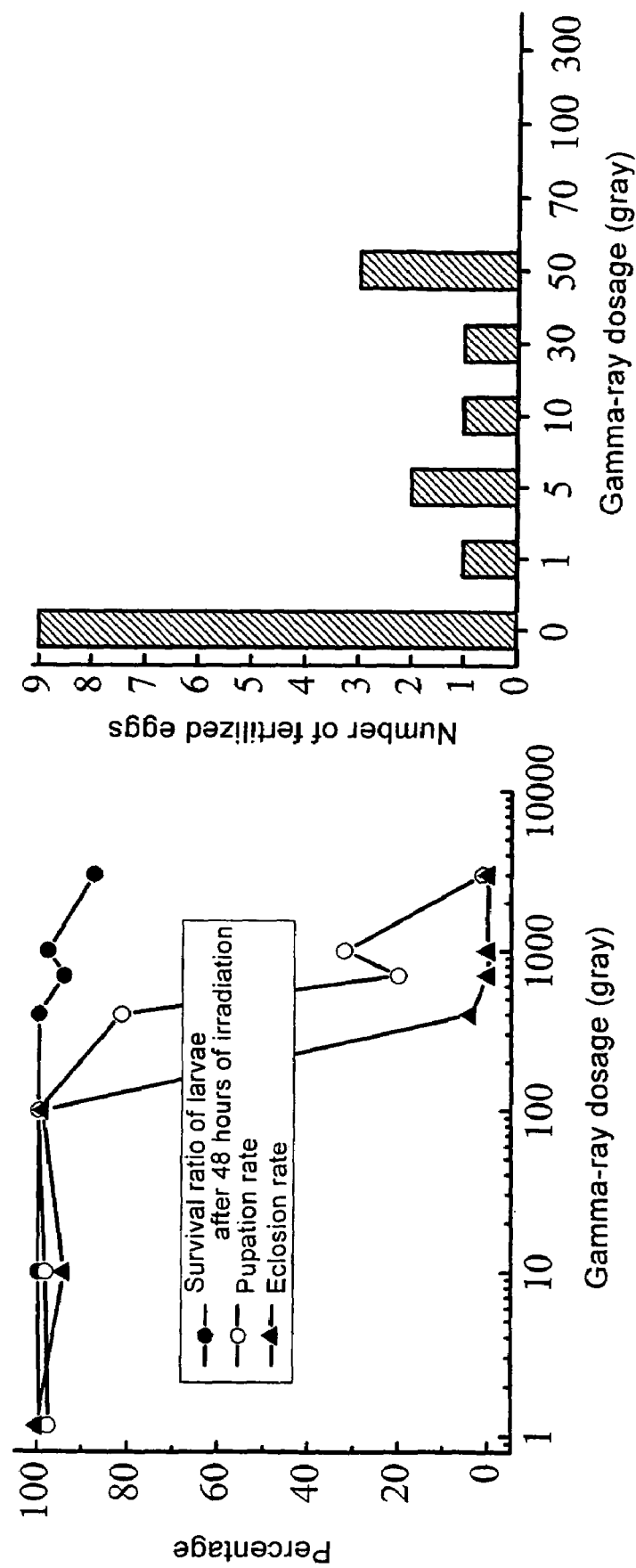
FIG. 7 shows the effects of the application of gamma rays upon the larvae of *Polypedilum vanderplanki*.

FIG. 7 shows the results of such inspection. The larval survival ratio was not affected by gamma-ray application of 3,000 gray 48 hours later. In contrast, the eclosion rate was not affected by gamma-ray application of 100 gray, but eclosion was inhibited by gamma-ray application of 400 gray. No fertilized egg was obtained with a dose higher than 50 gray.

Accordingly, it was demonstrated that the larvae of *Polypedilum vanderplanki* had been sterilized via gamma-ray application of 50 gray or higher. Thus, the risk of ecosystem disruption resulting from escape of African *Polypedilum vanderplanki* could be completely avoided.

INDUSTRIAL APPLICABILITY

According to the present invention, sterilized and dehydrated insect larvae that would not disrupt the environment can be effectively produced. The produced insect larvae can be utilized as educational materials or the like, and this can allow for easy observation of the mysteries of life and extraordinary stress tolerance.

The invention claimed is:

1. A method for dehydrating *Polypedilum vanderplanki* larvae comprising:
   gradually reducing the humidity until said larvae are dehydrated and enter a cryptobiotic state, and
   applying a gamma ray dose of 50 gray or higher to the dehydrated larvae.

2. The method of claim 1, further comprising desiccating said dehydrated larvae.

3. The method of claim 1 which is carried out in a single vessel which contains said larvae.

4. The method of claim 1, comprising reducing the humidity in at least three separate stages to obtain the dehydrated larvae.

5. The method of claim 1, wherein the larvae are dehydrated at least by exposure to a humidity of 5% or less for at least 1 day.

6. The method of claim 1, wherein the humidity is reduced in at least three separate stages, wherein said stages comprise: (i) keeping humidity at 100% for 1 day, (ii) reducing the humidity to 55% to 95% for a day, and (iii) dehydrating the larvae from (ii) at a humidity of 5% or less for at least 1 day.

7. The method of claim 1, wherein the larvae are dehydrated to the extent that water constituting 80% of the larvae bodies is lost.

8. The method of claim 1, further comprising packaging the larvae for shipment or storage.

9. An educational material comprising dehydrated *Polypedilum vanderplanki* larvae prepared by the method of claim 1.

10. A method for reviving *Polypedilum vanderplanki* larvae from a cryptobiotic state comprising contacting dehydrated larvae produced by the method of claim 1 with water.

* * * * *